US006024568A

United States Patent [19]
Mathiesen

[11] Patent Number: 6,024,568
[45] Date of Patent: *Feb. 15, 2000

[54] MASTER DIAGNOSTIC MODEL FOR TEETH

[75] Inventor: Ole H. Mathiesen, Vadnais Heights, Minn.

[73] Assignee: Valley Dental Arts, Stillwater, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/800,697

[22] Filed: Feb. 14, 1997

[51] Int. Cl.$^7$ ...................................................... A61C 5/00
[52] U.S. Cl. ........................................... 433/213; 433/229
[58] Field of Search ................................. 433/213, 217.1, 433/229, 26

[56] References Cited

U.S. PATENT DOCUMENTS

| | | |
|---|---|---|
| 3,971,133 | 7/1976 | Mushabac . |
| 4,288,472 | 9/1981 | Jorgensen ................................. 433/213 |
| 4,745,961 | 5/1988 | Salandra ................................... 433/213 |
| 4,973,251 | 11/1990 | Golub ..................................... 433/217.1 |

OTHER PUBLICATIONS

Heraeus Kulzer, Palaseal—Product information sheet, Jul. 1996.
Brochure "Willi Geller Creation, The Ultimate in Aesthetic Porcelain", Jensen Industries Incorporated, No date.
DIN Safety data sheet for Palaseal, Heraeus Kulzer, No date.

*Primary Examiner*—Ralph A. Lewis
*Attorney, Agent, or Firm*—Oppenheimer Wolff & DonnellyLLP; Chad A. Klingbeil

[57] ABSTRACT

The present invention includes a diagnostic model for representin the in situ position and status of an individual's teeth. The model comprises a synethic wax substrate representing soft gum tissue of the individual. The model also includes a synethic tooth defined by the wax, gum tissue substrate wherein the tooth comprises a wax tooth form that is overlaid with an acrylic-like resin substantially free of a filler having properties of wetability and brittleness.

The present invention also includes a method for making a provisional model of human teeth. The method includes providing a substrate for representing pink tissue of an individual's mouth. A tooth is prepared by molding a tooth shaped in wax and overlaying the wax with a substantial unfilled acrylic-like resin having properties of wetability and brittleness. The tooth is an integral part of the substrate.

6 Claims, 1 Drawing Sheet

MASTER DIAGNOSTIC MODEL FOR TEETH

BACKGROUND OF THE INVENTION

The present invention relates to a diagnostic model for teeth and to a method for making the diagnostic model.

Preparation of a dental prosthesis requires a dentist or oral surgeon to make an impression of a patient's teeth. The impression may be of the patient's teeth in the patient's upper jaw or teeth in the patient's lower jaw or teeth in both the upper jaw and the lower jaw. The impression is typically made with a polymeric material that has a soft consistency when the impression is made but that rapidly hardens once removed from the patient's mouth. The impression is a negative impression in that the teeth are represented by cavities within the polymeric material.

Individuals creating a dental prosthesis work with the impression and build a master diagnostic model. This master diagnostic model is a representation of the patient's existing teeth and also serves as a model for any new prosthetic device or devices.

The diagnostic model typically includes a pink wax substrate in order to represent pink tissue of the patient's gums and an ivory wax substrate in order to represent the patient's teeth. Unfortunately, the wax teeth lack the luster, color and hardness of natural teeth and therefore do not look or feel like the final prosthetic teeth that the patient ultimately receives. However, because the model is provisional, prostheses manufacturers have not prepared more accurate models due to excessive cost.

SUMMARY OF THE INVENTION

The present invention includes a diagnostic model for representing the in situ position and status of an individual's teeth. The model comprises a synthetic wax substrate representing soft gum tissue of the individual. The model also includes a synthetic tooth defined by the wax, gum tissue substrate wherein the tooth comprises a wax tooth form that is overlaid with an acrylic-like resin substantially free of a filler having properties of wetability and brittleness.

The present invention also includes a method for making a provisional model of human teeth. The method includes providing a substrate for representing pink tissue of an individual's mouth. A tooth is prepared by molding a tooth shape in wax and overlaying the wax with a substantially unfilled acrylic-like resin having properties of wetability and brittleness. The tooth is an integral part of the substrate.

DETAILED DESCRIPTION OF PREFERRED EMBODIMENTS

Figure 1:
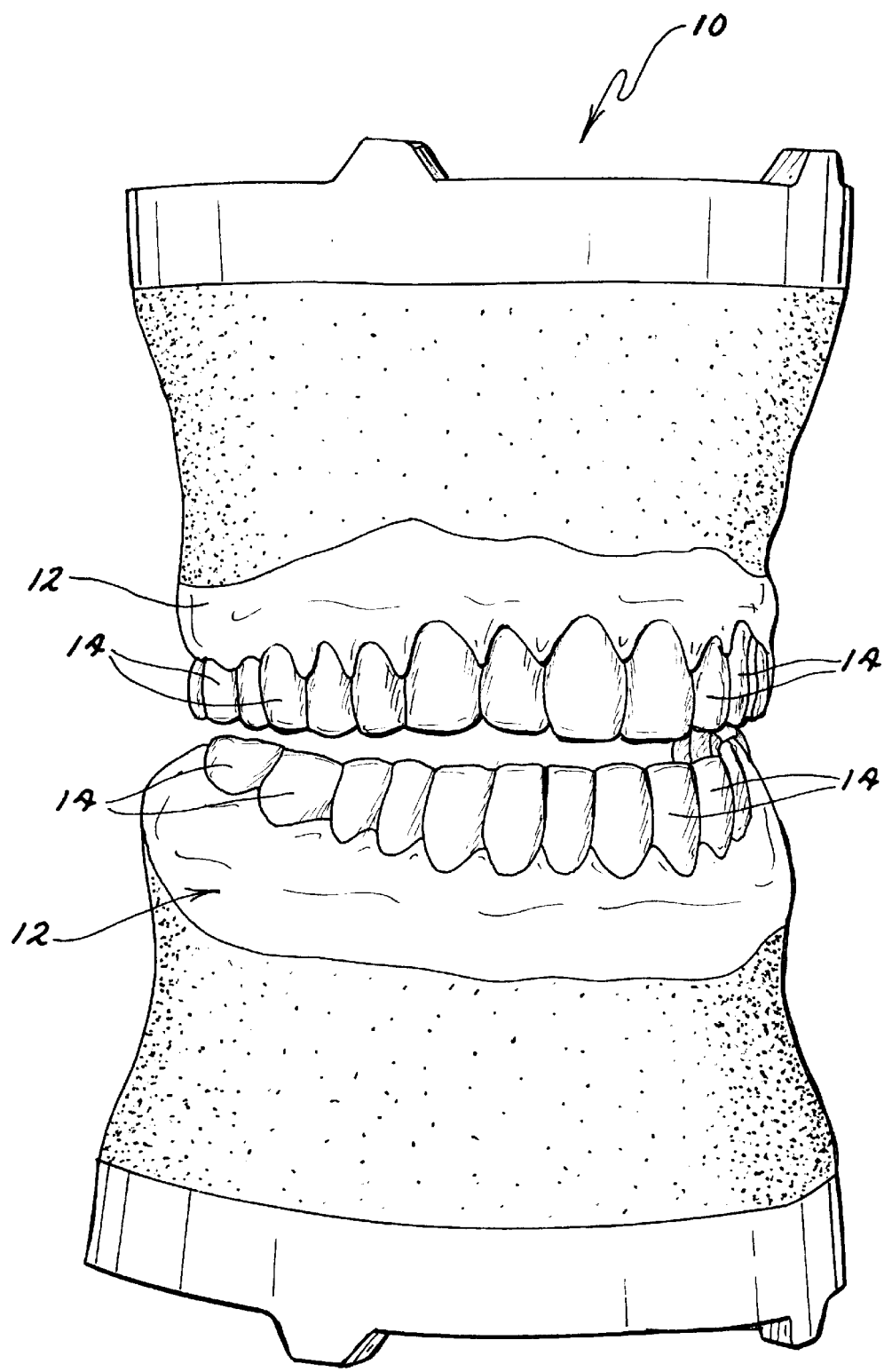
FIG. 1 shows one perspective view of a provisional diagnostic model of the present invention.

The present invention includes a provisional diagnostic model indicated generally at 10 in FIG. 1 for representing an individual's teeth that includes a synthetic substrate 12 representing soft pink gum tissue of an individual's mouth and at least one tooth 14 extending from the substrate 12. The tooth includes a wax representation of the individual's tooth that is overlaid with an acrylic-like resin substantially free of filler having a wetability and brittleness that more closely approximates that of tooth enamel than wax. In one preferred embodiment, the resin is a PalaSeal resin and the wax is Creare wax.

Prior to development of the model of the present invention, master provisional diagnostic models were made entirely of wax. Although the models served a function of illustrating the position of a dental prosthesis in an individual's mouth and to a limited degree the special interaction of the prosthesis with the individual's teeth, the model did not serve in illustrating aesthetic and mechanical aspects of the interplay between the prosthesis and the individual's teeth. Wax, as a material, lacks the luster, wetability and strength required to provide a more representational model of a tooth. Further, because both the soft tissue and the tooth representations were made of wax, the appearance of the teeth could not be differentiated from the pink wax other than by a difference in color. Additionally, a wax tooth, unlike a natural tooth, readily deforms when subjected to a force such as the weight of the prosthesis.

It has surprisingly been found that the use of a substantially unfilled acrylic-like resin, such as PalaSeal, as a coating, imparts a natural tooth appearance. The results are surprising because filled acrylic resin does not produce desired results. Furthermore, an all acrylic tooth does not produce desired results.

In the model of the present invention, the underlying gum tissue substrate remains a wax substrate. However, the teeth are imparted with a more natural appearance and strength by application of a particular type of unfilled resin to a wax embodiment of each tooth of the model. Upon application of the unfilled PalaSeal resin, the teeth acquire a wetability and brittleness closely resembling that of a natural tooth. As a consequence of the more representational model, manufacturers of dental prostheses can make a prosthesis that will ultimately have an improved compatibility with the patient's existing teeth. This is, in part because the prosthesis can be positioned in a manner that more accurately represents its positioning in the patient's mouth.

Because the substantially unfilled resin is applied to the surface of a wax tooth, additional material costs in making the model are minimized. Further, because the resin application is a coating-type application, the resin may be applied merely by brushing or spraying onto the wax tooth. It is not necessary to develop a new manufacturing process for making the foundation of the model tooth structure.

In one preferred embodiment, the teeth are made with an ivory wax such as Creare wax manufactured by Leach & Dillon of Cranston, Rhode Island. Creare wax is a paraffin wax with a specific gravity of about 0.8 to 0.8 grams per cubic centimeter. A white to ivory color is preferred The wax has a flash point of 425° F.

The teeth are overlaid by a resin such as a PelaSeal resin manufactured by Heraeus Kulzer of Irving, Calif. PelaSeal resin is a light curing lacquer preparation on the basis of methyl methacrylate and methacrylated reactive resins. PelaSeal has a density of 1.1 grams per cubic centimeters at 23 degrees Centigrade. PelaSeal has a solubility in water of 16 grams per liter and a viscosity of 11 to 12 s in a Ford Bowl, 4 millimeters, at 23 degrees Centigrade.

Each of the wax and the resin are prepared in a manner known to those skilled in the art. The resin is prepared so as to have a consistency that lends it to application with a brush or by a spray. Once applied, the resin is dried by air drying.

Although the present invention has been described with reference to preferred embodiments, workers skilled in the art will recognize that changes may be made in form and detail without departing from the spirit and scope of the invention.

What is claimed is:

1. A diagnostic model for use outside of an individual's body for representing an in situ position and status of the individual's teeth, comprising:

a synthetic wax main body substrate that comprises a wax substrate portion representing soft tissue of the individual; and a synthetic tooth substrate portion wherein the synthetic tooth substrate portion comprises a wax tooth form that is overlaid with an acrylic-like unfilled resin.

2. The device of claim 1 wherein the resin is an unfilled acrylic-like resin.

3. The device of claim 1 wherein the resin includes methyl methacrylate.

4. A method for making a model for human teeth, comprising:

providing a main body wax substrate;

molding and coloring a portion of the main body substrate in order to simulate pink tissue of an individual's mouth; and preparing a tooth by molding a tooth shape in the wax main body substrate and overlaying the wax with an acrylic-like unfilled resin imparting properties of wetability and brittleness to the tooth shape thereby simulating the in situ appearance of the tooth in the main body substrate.

5. The method of claim 4 wherein the unfilled resin is an acrylic-like unfilled resin.

6. The method of claim 4 wherein the substrate is wax.

\* \* \* \* \*